United States Patent
Perng et al.

(10) Patent No.: US 10,960,126 B2
(45) Date of Patent: Mar. 30, 2021

(54) PORTABLE DEVICE FOR MONITORING VASCULAR ACCESS STATUS

(71) Applicants: NEXCOM International Co., Ltd., New Taipei (TW); Vesstone Co., Ltd., Taipei (TW)

(72) Inventors: Chiy-Ferng Perng, New Taipei (TW); Yi-Chung Chen, New Taipei (TW); Cheng-Jen Wang, New Taipei (TW); Tzong-yann Lee, Taipei (TW)

(73) Assignees: NEXCOM INTERNATIONAL CO., LTD., New Taipei (TW); VESSTONE CO., LTD., Taipei (TW)

( * ) Notice: Subject to any disclaimer, the term of this patent is extended or adjusted under 35 U.S.C. 154(b) by 359 days.

(21) Appl. No.: 15/666,403

(22) Filed: Aug. 1, 2017

(65) Prior Publication Data

US 2018/0326142 A1    Nov. 15, 2018

(30) Foreign Application Priority Data

May 12, 2017    (TW) .................................. 106115866

(51) Int. Cl.
*A61M 1/36* (2006.01)
*A61B 5/15* (2006.01)
(Continued)

(52) U.S. Cl.
CPC ....... *A61M 1/3656* (2014.02); *A61B 5/15003* (2013.01); *A61B 5/155* (2013.01);
(Continued)

(58) Field of Classification Search
CPC .... A61M 1/14; A61M 1/3653; A61M 1/3656; A61M 1/3658; A61M 1/3663;
(Continued)

(56) References Cited

U.S. PATENT DOCUMENTS 6,090,048 A *    7/2000    Hertz ................ A61M 5/16859
                                                                    600/485
6,623,443 B1    9/2003    Polaschegg
(Continued)

FOREIGN PATENT DOCUMENTS

CN    101022765 A    8/2007
CN    101784232 A    7/2010
(Continued)

OTHER PUBLICATIONS

Office Action dated Apr. 18, 2018 of the corresponding Taiwan patent application No. 106115866.
(Continued)

*Primary Examiner* — Philip R Wiest
(74) *Attorney, Agent, or Firm* — Chun-Ming Shih; HDLS IPR Services

(57) ABSTRACT

A portable device for monitoring vascular access status is disclosed. The portable device comprises a measurement device and a monitoring module. The measurement device senses vibration data induced by blood flow over certain part of a vascular access of a subject via a vibration-sensing module, and sends the sensed data to outside via its communication module. The monitor module controls an electronic device to receive the sensed data and determines a vibration evaluation index corresponding to a status of the part of the vascular access. The portable device for monitoring vascular access status of the present disclosed example has advantages of small size, easy to carry, low cost, and so on, so as to be applicable to home vascular access status monitor.

15 Claims, 8 Drawing Sheets

(51) Int. Cl.
*A61M 5/42* (2006.01)
*A61B 5/155* (2006.01)
*A61B 5/153* (2006.01)
*A61M 1/14* (2006.01)

(52) U.S. Cl.
CPC ........ *A61B 5/1535* (2013.01); *A61B 5/15087* (2013.01); *A61B 5/150748* (2013.01); *A61B 5/150992* (2013.01); *A61M 1/14* (2013.01); *A61M 1/3663* (2013.01); *A61M 5/427* (2013.01); *A61M 2205/3334* (2013.01); *A61M 2205/3375* (2013.01); *A61M 2205/3569* (2013.01); *A61M 2205/3584* (2013.01)

(58) Field of Classification Search
CPC ............ A61B 5/15003; A61B 5/15078; A61B 5/15087; A61B 5/150992; A61B 5/1535; A61B 5/155
See application file for complete search history.

(56) References Cited

U.S. PATENT DOCUMENTS

| | | | |
|---|---|---|---|
| 7,527,597 B2 | 5/2009 | Sandler et al. | |
| 8,152,751 B2 | 4/2012 | Roger et al. | |
| 8,603,020 B2 * | 12/2013 | Roger | A61M 1/3653 604/4.01 |
| 2002/0099286 A1 | 7/2002 | Sandler et al. | |
| 2003/0128126 A1 * | 7/2003 | Burbank | A61M 1/367 340/605 |
| 2004/0249293 A1 * | 12/2004 | Sandler | A61B 7/00 600/481 |
| 2009/0088612 A1 | 4/2009 | Bouton | |
| 2013/0292319 A1 * | 11/2013 | Fulkerson | A61M 1/3626 210/321.78 |

FOREIGN PATENT DOCUMENTS

| | | |
|---|---|---|
| TW | I538658 | 6/2016 |
| TW | 201626941 A | 8/2016 |
| TW | 201634004 A | 10/2016 |
| WO | 2012163738 A1 | 12/2012 |

OTHER PUBLICATIONS

Office Action dated May 28, 2020 of the corresponding China patent application No. 201710360786.1.

* cited by examiner

US 10,960,126 B2

PORTABLE DEVICE FOR MONITORING VASCULAR ACCESS STATUS

BACKGROUND OF THE INVENTION

Field of the Invention

The technical field relates to vascular access status monitor, and more particularly related to portable device for monitoring vascular access status.

Description of Related Art

The patient having the disease of losing renal function or having incomplete renal function must accept hemodialysis which transfusing the patient's blood to a hemodialysis machine via the vascular access for filtering the metabolic waste in the blood. Above-mentioned vascular access can be formed by surgery, and can be used to transfuse out the patient's blood from the patient's body to the hemodialysis machine and transfuse back the filtered blood from the hemodialysis machine to the patient's body.

In general, there are two types of the vascular accesses formed by surgery, one is the arteriovenous fistula (AVF), and another is the arteriovenous graft (AVG).

Please refer to FIG. 1A, which is a schematic view of arteriovenous graft. The arteriovenous graft 14 may be an artificial plastic tube which one end is connected to the arteries 12, and another end is connected to the veins 10. Please refer to FIG. 1B, which is a schematic view of arteriovenous fistula. The arteriovenous fistula 16 is directly connected to the arteries 12 and the veins 10.

Each of above-mentioned vascular accesses has a possibility of becoming stenotic or thrombosed. When the vascular access becomes stenotic or thrombosed, the effect of hemodialysis becomes bad, and the stenotic or thrombosed vascular accesses has a possibility of harming the patient's live if the vascular accesses is seriously stenotic or thrombosed. Thus, the vascular access status monitor has become a critical issue.

The vascular access status monitor of the related art retrieves the ultrasound images via an ultrasonic image capture device which has big size and high cost, and calculates the blood flow of the vascular access. After this, the professional medical staff can diagnose a vascular access status according to the ultrasonic images.

Because of being limited by the ultrasonic image capture device which has big size and high cost and the professional medical staff's diagnosis, the vascular access status monitor of the related art is not applicable to home self-monitor, and is not conducive to early detect that the vascular access status becomes bad.

SUMMARY OF THE INVENTION

The object of the present disclosed example is to provide a portable device for monitoring vascular access status, the device is arranged a vibration-sensing module with small size and low cost for replacing the ultrasonic image capture device and executing vascular access status monitor.

One of the present disclosed examples, a portable device for monitoring vascular access status, comprises a measurement device and a monitoring module. The measurement device comprises a vibration-sensing module and a communication module. The vibration-sensing module senses vibration data induced by blood flow over a part of a vascular access of a subject. The communication module is electrically connected to the vibration-sensing module and is used to transmit data to outside. The monitoring module controls an electronic device connected to the communication module of the measurement device to load vibration threshold data corresponding to the sensed part of the vascular access and determine a vibration evaluation index corresponding to a status of the part of the vascular access according to the vibration data and vibration threshold data.

The portable device for monitoring vascular access status of the present disclosed example has advantages of small size, easy to carry, low cost, and so on, so as to be applicable to home vascular access status monitor.

BRIEF DESCRIPTION OF DRAWING

The features of the present disclosed example believed to be novel are set forth with particularity in the appended claims. The present disclosed example itself, however, may be best understood by reference to the following detailed description of the present disclosed example, which describes an exemplary embodiment of the present disclosed example, taken in conjunction with the accompanying drawings, in which:

DETAILED DESCRIPTION OF THE INVENTION

In cooperation with attached drawings, the technical contents and detailed description of the present disclosed example are described thereinafter according to a preferable embodiment, being not used to limit its executing scope. Any equivalent variation and modification made according to appended claims is all covered by the claims claimed by the present disclosed example.

Figure 1A:
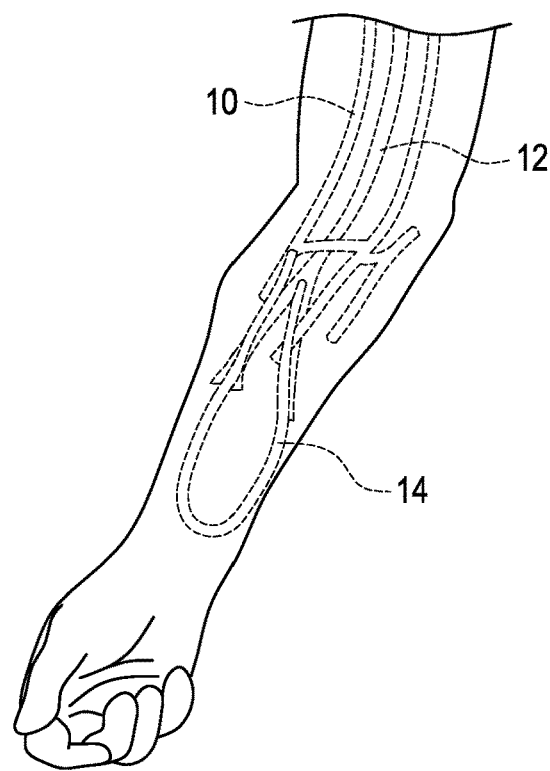
FIG. 1A is a schematic view of arteriovenous graft.
Figure 1B:
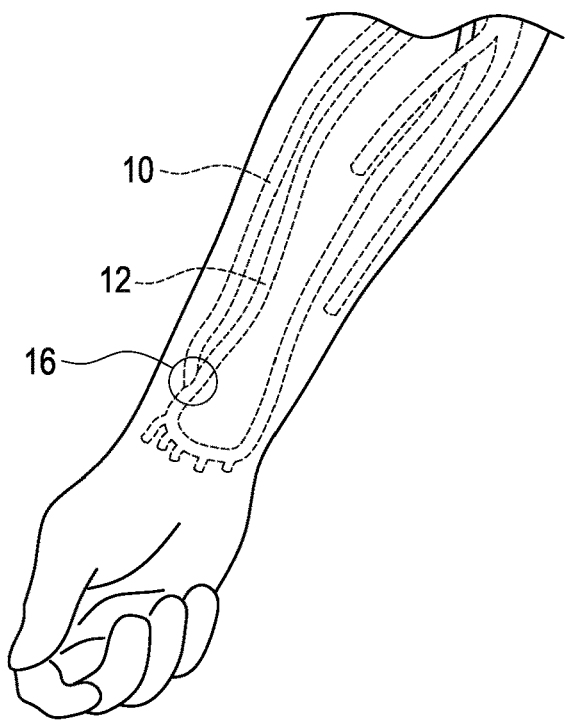
FIG. 1B is a schematic view of arteriovenous fistula.
Figure 2:
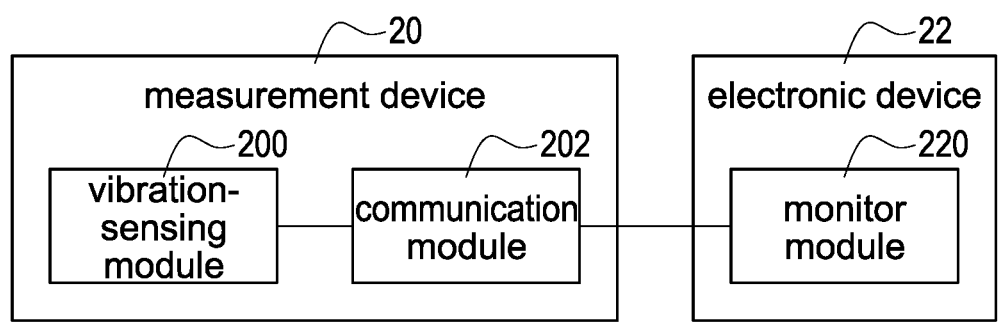
FIG. 2 is an architecture diagram of a portable device for monitoring vascular access status according to the first embodiment of the present disclosed example.

Please refer to FIG. 2, which is an architecture diagram of a portable device for monitoring vascular access status according to the first embodiment of the present disclosed example.

The portable device 2 for monitoring vascular access status (hereinafter the monitor device) mainly comprises a measurement device 20 and a monitor module 220. The measurement device 20 comprises a vibration-sensing module 200 and a communication module 202.

The vibration-sensing module 200, such as one or more three-axis accelerometer(s), force sensor(s) or other types of vibration sensors, is used to sense the vibrations induced by blood flow over certain part of a vascular access (such as veins, arteries, arteriovenous fistula or arteriovenous graft) of a subject, and generate vibration data corresponding to the certain part.

The communication module 202, such as Bluetooth network module, ZigBee network module, Wi-Fi network module, infrared network module or other types of wireless transmitters or serial communication modules, is used to connect to an electronic device 22, and transfer data (such as vibration data) to the electronic device 22.

In one embodiment, the communication module 202 may comprise a microcontroller unit (MCU); above-mentioned MCU is used to control the measurement device 20 and process data or signal.

The monitor module 220, such as MCU or processor, is arranged in the electronic device and used to control the electronic device 22. More specifically, the monitor module 220 may control the electronic device 22 to receive above-mentioned vibration data from the communication module 202, and determine an evaluation index corresponding to a status of the certain part of the vascular access.

Please be noted that the status determined according to the vibrations induced by blood flow may have possibility of error because the blood flow velocity and the blood pressure of each subject are different, such that the determined diagnostic result has possibility of error. This error may make the patient delay to accept treatment. As a result, the present disclosed example may not provide the diagnostic result directly according to the sensed data, but determine the evaluation index of this inspection of the subject instead. Thus, the subject (or the monitor module 202) may determine by himself/herself the actual status of the subject's vascular access according to long-term variation of the evaluation indexes.

Please be noted that there are continuous thrills induced by blood flow over a junction of blood vessels when the vascular access is normal and healthy (no stenosis, no blockade). Besides, there are only the pulsations or weak thrills induced by blood flow when the vascular access is not normal and healthy (having stenosis or blockade). The present disclosed example is to determine whether the thrills disappears or is weak via analyzing the vibration data induced by blood flow, and further determines the evaluation index of the status of the vascular access.

Please be noted that although the status of the vascular access can only be one of the two status, "blockade" or "non-blockade", in general cognition, consider above-mentioned diagnostic result error, the present disclosed example defines a designated value scope constituted by a plurality of continuous values, and defines that the two-end of the value scope are respectively positive index (for example, the index is more close to 1, the possibility of non-blockade is higher.) and negative index (for example, the index is more close to 10, the possibility of blockade is higher.). Thus, the subject (or the monitor module 202) can determine that the status of the subject's vascular access may be bad when the evaluation index of the subject changes towards negative index many times (such as changing from 6 to 9). The subject (or the monitor module 202) can determine that the evaluation index is the normal value of the subject when the evaluation index of the subject remains fixed index many times (such as remaining on 8).

Compare to the related art which uses the ultrasonic image capture device having big size and high cost and rely on the diagnosis of the professional medical staff to execute the vascular access status monitor, the portable device for monitoring vascular access status of the present disclosed example has following advantages of small size, easy to carry, low cost and so on because of only using the vibration-sensing module. Besides, the present disclosed example can determine the evaluation index of the vascular access automatically, and is applicable to home vascular access status monitor.

Figure 3A:
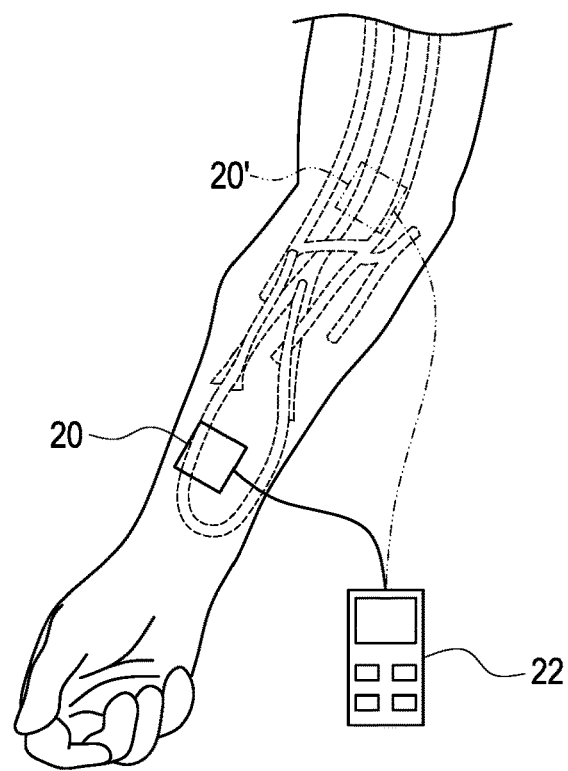
FIG. 3A is a schematic view of using a portable device for monitoring vascular access status over arteriovenous graft according to the second embodiment of the disclosed example.
Figure 3B:
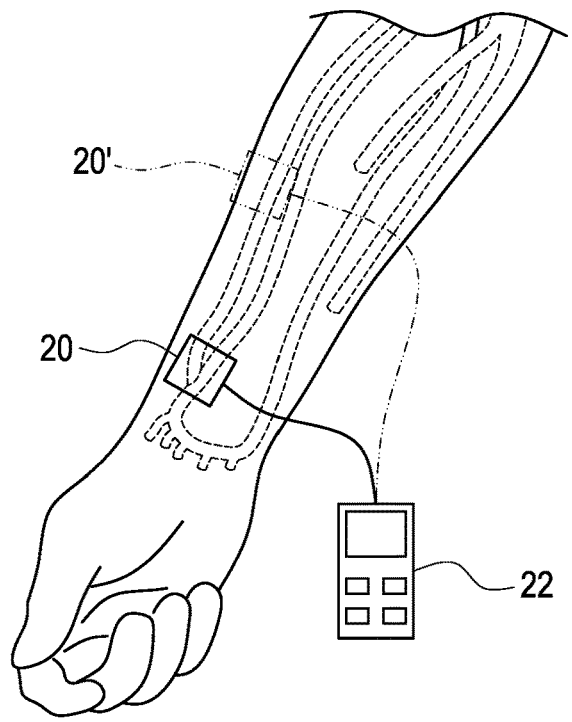
FIG. 3B is a schematic view of using a portable device for monitoring vascular access status over arteriovenous fistula according to the second embodiment of the disclosed example.

Please refer to FIG. 2, FIG. 3A and FIG. 3B simultaneously, FIG. 3A is a schematic view of using a portable device for monitoring vascular access status over arteriovenous graft according to the second embodiment of the disclosed example, FIG. 3B is a schematic view of using a portable device for monitoring vascular access status over arteriovenous fistula according to the second embodiment of the present disclosed example.

In this embodiment, the measurement device 20 may be used to sense the vibration data induced by blood flow over any part of the vascular access of the subject. Besides, the electronic device 22 is a device designed for the measurement device 20 (namely, the measurement device 20 and the electronic device 22 must be used together), and the electronic device 22 is connected to the measurement device 20 via wire. Besides, in this example, the measurement device 20 may further comprise a patch structure, the patch structure is used to removably paste over the external part of the vascular access.

As shown in FIG. 3A and FIG. 3B, the subject can paste by himself/herself the measurement device 20 on the certain part of the vascular access of the subject (such as the position of the measurement device 20 shown in figures, the certain part is the position of arteriovenous graft in FIG. 3A, and the position of arteriovenous fistula in FIG. 3B) for a first measurement time (such as 30 seconds) for making the measurement device 20 sense the vibration data induced by blood flow over the certain part continuously when measurement. Or, the subject can paste by himself/herself the measurement device 20 on another part of the vascular access of the subject (such as the position of the measurement device 20 shown in figures, the part is the position of veins in FIG. 3A and FIG. 3B) for a second measurement time (such as 50 seconds) for making the measurement device 20 sense another vibration data induced by blood flow over another part continuously Besides, the measurement device transfers the sensed vibration data to the electronic device 22 for analysis and process real-time or after sensing.

Finally, the monitor module 220 controls the electronic device 22 to receive above-mentioned vibration data (namely, the vibration data of each part of vascular access), retrieves the vibration threshold data respectively corresponding to each part of vascular access, and determines each evaluation index respectively corresponding to the current status of each part of vascular access according to each vibration data and the corresponded vibration threshold data.

Although the monitor module 220 in above-mentioned embodiments are implemented in the way of hardware, but this specific example is not intended to limit the scope of the present disclosed example. In the other embodiment, the monitor module 220 may be implemented in the way of software.

Figure 4:
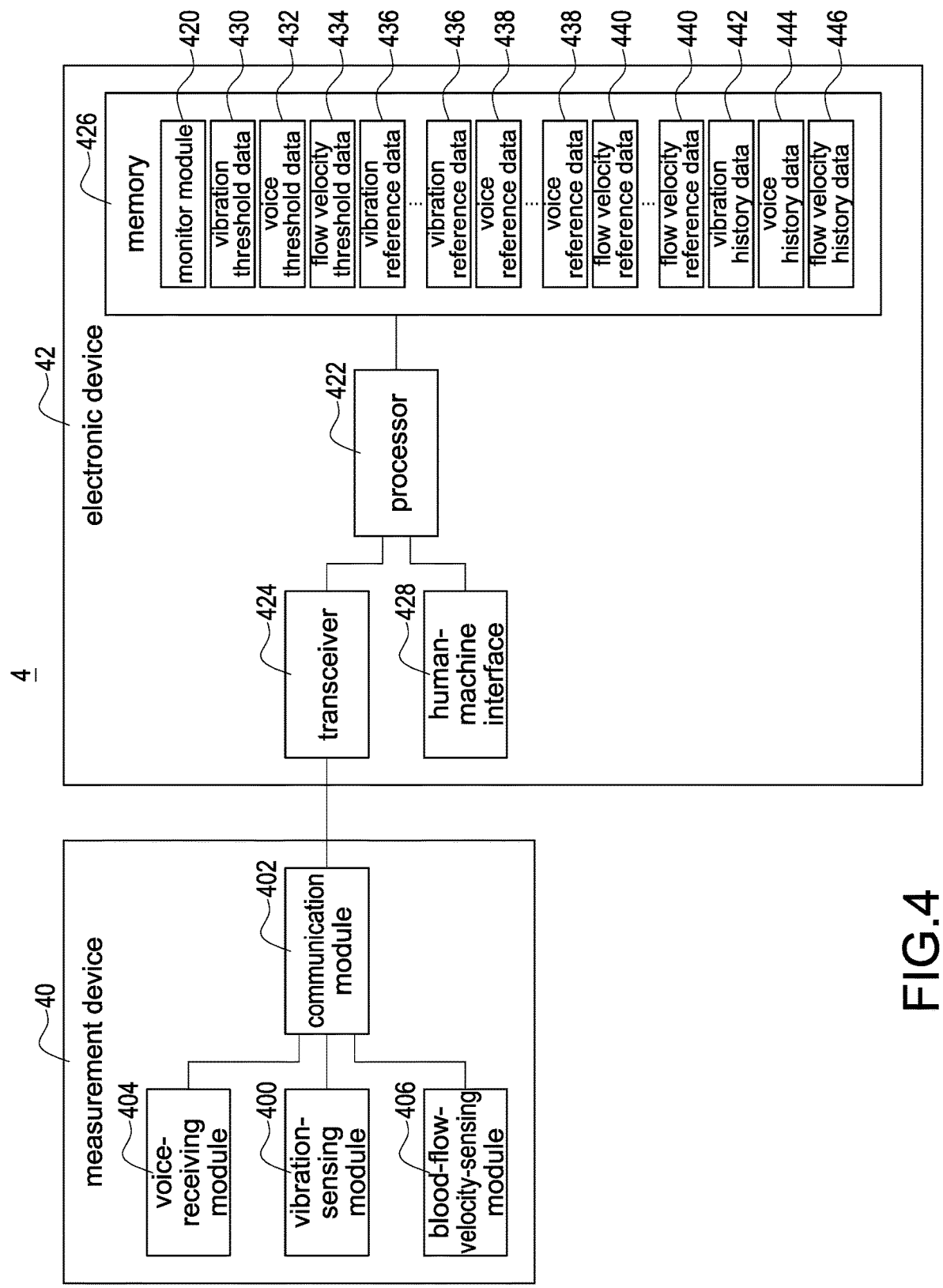
FIG. 4 is an architecture diagram of a portable device for monitoring vascular access status according to the third embodiment of the present disclosed example.

Please refer to FIG. 4, which is an architecture diagram of a portable device for monitoring vascular access status according to the third embodiment of the present disclosed example. The portable device for monitoring vascular access status 4 (hereinafter the monitor device 4), the measurement device 40, the vibration-sensing module 400, the communication module 402, and the electronic device 42 shown in FIG. 4 are respectively same as or similar to the monitor device 2, the measurement device 20, the vibration-sensing module 200, the communication module 202, and the electronic device 22 of the embodiment shown in FIG. 2, the relevant description is omitted for brevity.

In one embodiment, measurement device 40 further comprises one or more voice-receiving module(s) 404 (such as one or more omnidirectional microphone(s), directional microphone(s) or other types of microphone(s)) electrically connected to communication module 402. The voice-receiving module 404 is used to record the voice induced by blood flow over certain part of the vascular access of the subject, and generate the corresponded voice data, wherein the sensible voice frequency range of the voice-receiving module 404 is similar to or falls within the human audible frequency range.

In one embodiment, the voice-receiving module 404 comprises an audio amplifier and/or an audio filter (not shown in figure). The audio amplifier is used to amplify the volume of the sensed voice data, the audio filter us used to filter out the noise from the sensed voice data. Furthermore, because the voice induced by blood flow is quite weak and there may be a lot of interference voice sources in the measurement environment, the present disclosed example can effectively amplify volume and filter out noise via using the audio amplifier and the audio filter to execute pre-process to the sensed voice data, so as to improve the accuracy of following determination.

In one embodiment, the measurement device 40 further comprises a blood-flow-velocity-sensing module 406 electrically connected to the communication module 402. The blood-flow-velocity-sensing module 406 is used to sense flow velocity of blood flow over certain part of the vascular access of the subject, and generate the corresponded flow velocity data. Preferably, the blood-flow-velocity-sensing module 406 is an optical flow velocity meter, such as on or more laser Doppler tachometer (s).

Besides, the electronic device 42 is a general-purpose device, such as smart phone, notebook, wearable device, cloud host, or other types of multifunctional electronic devices, and comprises a transceiver 424, a memory 426, a human-machine interface 428 and a processor electrically connected to above-mentioned element.

The transceiver 424 and the communication module 402 use the compatible communication technology, such as Bluetooth communication, so as to have ability of communicating with each other. The memory 426 is used to store data. The human-machine interface 428, such as indicator light, speakers, microphones, buttons, touch screens, or any combination of the above-mentioned devices, is used to accept user operation or output data. The processor is used to control the electronic device 42.

Besides, on this embodiment, the monitor module 420 is a computer program stored in the computer-readable non-transitory memory 426. The computer program comprises computer-executable codes. After the processor 42 executes the codes of the monitor module 420, the processor 42 can be configured to execute with the measurement device 40 each step of the method of monitoring vascular access status of each embodiment of the present disclosed example.

Figure 6:
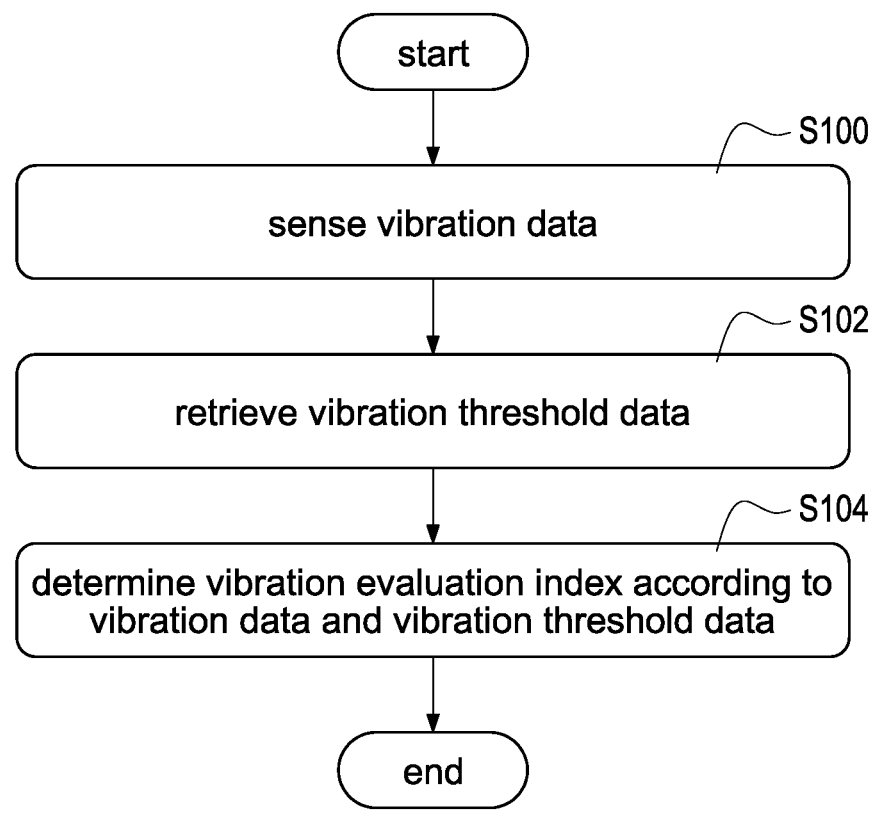
FIG. 6 is a flowchart of a method of monitoring vascular access status according to the first embodiment of the present disclosed example.

Please refer to FIG. 4 and FIG. 6 simultaneously; FIG. 6 is a flowchart of a method of monitoring vascular access status according to the first embodiment of the present disclosed example. In the embodiment shown in FIG. 6, the subject first pastes the measurement device 40 on an examination part of the vascular access for making the measurement device 40 sense the vibration data induced by blood flow over examination part via the vibration-sensing module 400 and transfer the sensed vibration data to outside (step S100).

Then, the electronic device 42 loads the pre-stored vibration threshold data 430 from the memory 426 (step S102). In one embodiment, the memory 426 stores a plurality of the vibration threshold data 430, each vibration threshold data 430 is respectively corresponded to the various part of the vascular access. The subject may configure the examination part being sensed this time via the human-machine interface 428, for making the electronic device 42 load the vibration threshold data 430 corresponding to the examination part being sensed this time automatically.

Finally, the electronic device 42 determines the vibration evaluation index corresponding to the status of the examination part according to the received vibration data and the loaded vibration threshold data 430 (step S104).

In one embodiment, the vibration threshold data is the reference vibration amplitude value corresponding to the normal status of the certain part of the vascular access of the subject. The electronic device 42 is configured to analyze a plurality of vibration amplitudes of the vibration data and calculate one representative amplitude (such as maximum or average of the vibration amplitudes), and compares the representative amplitude with the vibration threshold data. If the representative amplitude is less than the vibration threshold data, the electronic device 42 sets that the vibration evaluation index has a bias in negative index. Otherwise, the electronic device 42 sets that the vibration evaluation index has a bias in positive index.

The method of monitoring vascular access status of the present disclosed example can effectively measure the vibration induced by blood flow over the vascular access, and provide the vibration evaluation index of the vascular access, so as to making the subject infer the status of the vascular access accurately.

Figure 7:
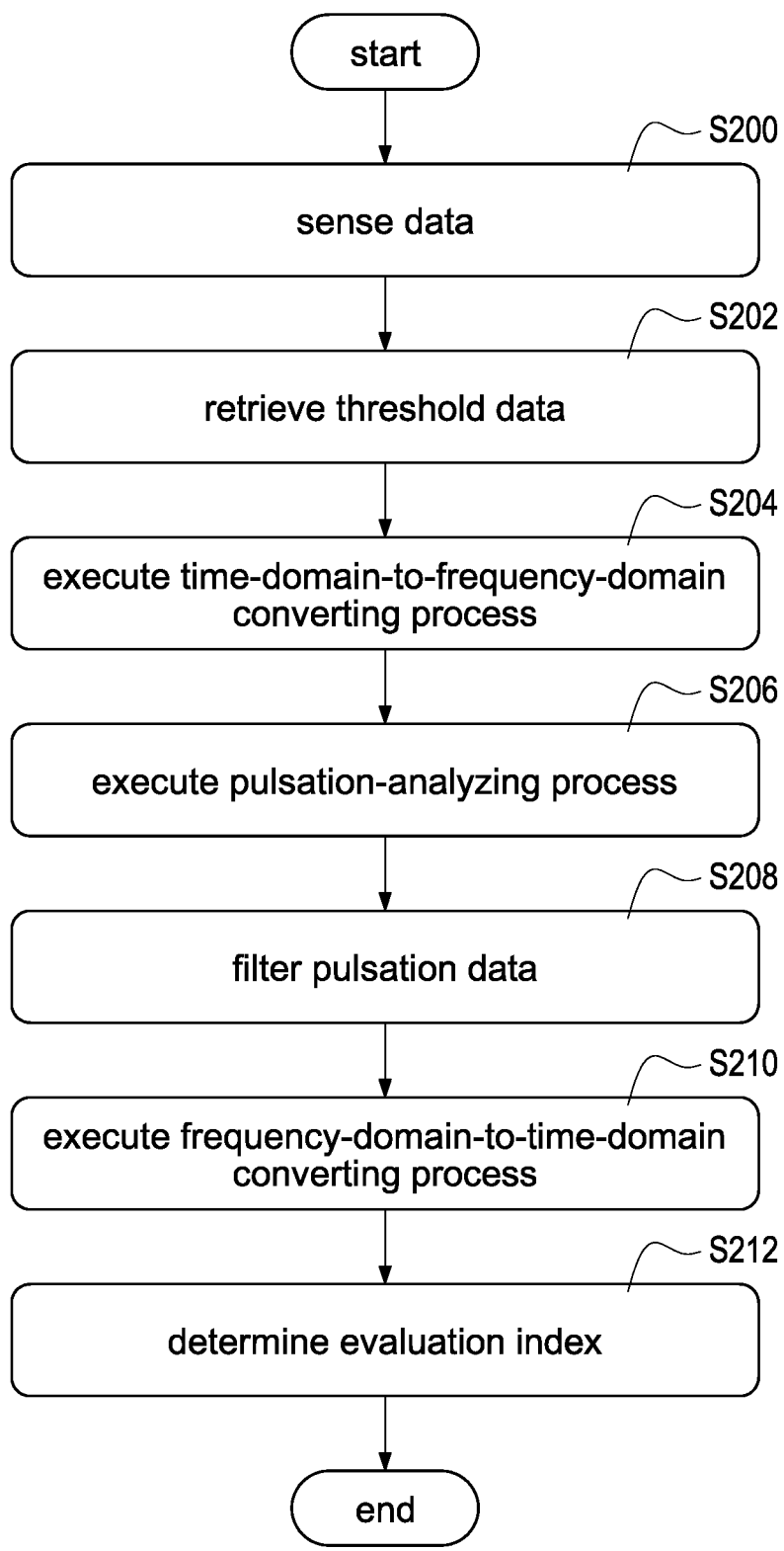
FIG. 7 is a flowchart of a method of monitoring vascular access status according to the second embodiment of the present disclosed example.

Please refer to FIG. 4 and FIG. 7 simultaneously; FIG. 7 is a flowchart of a method of monitoring vascular access status according to the second embodiment of the present disclosed example.

In the embodiment shown in FIG. 7, the monitor device 4 may measure the vibration data, the voice data and flow velocity data of the same part of the vascular access simultaneously, determine the vibration evaluation index, the voice evaluation index and the flow velocity evaluation index, and determine the whole evaluation index of the part of the vascular access according to the determined vibration evaluation index, the voice evaluation index and the flow velocity evaluation index.

Please be noted that although the monitor device 4 measures the vibration data, the voice data and flow velocity data of the same part of the vascular access simultaneously in this embodiment, but this specific example is not intended to limit the scope of the present disclosed example.

In the other embodiment, the monitor device may only measure one or two of the vibration data, the voice data and flow velocity data, and determines the corresponded evaluation index according to the measured data. For example, the monitor device 4 can only measure the vibration data and the voice data, determine the vibration evaluation index and the voice evaluation index, and determine the whole evaluation index according to the determined vibration evaluation index and the voice evaluation index.

In the embodiment shown in FIG. 7, the subject may paste the measurement device on the examination part of the vascular access for making the measurement device 40 sense the sensed data induced by blood flow over examination part of a vascular access (step S200).

In one embodiment, the measurement device 40 senses the vibration data of this examination part via the vibration-sensing module 400, senses the voice data of this examination part via the voice-receiving module 404, senses the flow velocity data of this examination part via the blood-flow-velocity-sensing module 406, and transfers the sensed vibration data, voice data and flow velocity data via the communication module 402.

Then, the electronic device 42 load the threshold data corresponding to this part form the memory 426 (step S202), such as the vibration threshold data 430, the voice threshold data 432 and the flow velocity threshold data 434.

In one embodiment, the memory 426 stores a plurality of the vibration threshold data 430, a plurality of the voice threshold data 432 and a plurality of the flow velocity threshold data 434. Each vibration threshold data 430, each voice threshold data 432 and each flow velocity threshold data 434 are respectively corresponded to the various parts of the vascular access. The electronic device 42 loads the vibration threshold data 430, the voice threshold data 432 and the flow velocity threshold data 434 corresponding to the examination part.

In one embodiment, before measurement, the Professional medical staff may operates sophisticated instruments, such as vibration-sensing module with higher sensitivity, to measure each part of the vascular access of the same subject for retrieving the vibration data, the voice data and the flow velocity data of each part of vascular access in the normal status, and make the retrieved vibration data, the voice data and the flow velocity data as the vibration threshold data 430, the voice threshold data 432 and the flow velocity threshold data 434.

In one embodiment, the memory 426 stores a plurality of reference data, such as a plurality of vibration reference data 436, a plurality of voice reference data 438, and a plurality of flow velocity reference data 440, each reference data is respectively corresponded to a combination of the various part of the vascular access and a set of various physiological parameter(s), such as height, weight, age, or any combination of above-mentioned parameters. The electronic device 42 is configured to select the corresponded reference data as the threshold data (such as the vibration threshold data 430, the vibration threshold data 432 and the flow velocity threshold data 434) according to the examination part and the set of physiological parameters of the subject.

In one embodiment, the memory 426 stores history data measured in advance of the subject, such as vibration history data 442, voice history data 444 and flow velocity history data 446. This history data is corresponded to the certain part of the vascular access. The electronic device 42 selects the history data corresponding to the same part as the threshold data, such as the vibration threshold data 430, the voice threshold data 432 and the flow velocity threshold data 434.

Then, the electronic device 42 executes a time-domain-to-frequency-domain converting process to the received sensed data for obtaining the corresponded spectrum data (step S204).

In one embodiment, the electronic device 42 may further execute a band-pass filtering process to the generated spectrum data for filtering out the other noise frequencies except specific frequency (such as the frequency corresponding to the thrill).

In one embodiment, the electronic device 42 may execute a time-domain-to-frequency-domain converting process (such as Fast Fourier transform, Laplace transform, or discrete wavelet transform) to the received vibration data, the received voice data and the received flow velocity data for obtaining the corresponded vibration spectrum data, the corresponded voice spectrum data and the corresponded flow velocity spectrum data, but this specific example is not intended to limit the scope of the present disclosed example.

In the other embodiment, the electronic device 42 may execute the time-domain-to-frequency-domain converting process only to the received vibration data and the received voice data for obtaining the vibration spectrum data and the voice spectrum data, the electronic device 42 may not execute the time-domain-to-frequency-domain converting process to the flow velocity data.

Then, the electronic device 42 executes a pulsation-analyzing process to the generated spectrum data for obtaining pulsation spectrum data (step S206).

Take the electronic device 42 executing the time-domain-to-frequency-domain converting process to the vibration data, the voice data and the flow velocity data for example, the electronic device 42 may recognize the frequency having the highest amplitude (fundamental frequency) respectively in the vibration spectrum data, the voice spectrum data and the flow velocity spectrum data, and respectively configure the recognized frequency and its frequency multiplication (harmonic) as the pulsation vibration spectrum data, pulsation voice spectrum data and pulsation flow velocity spectrum data.

In one embodiment, the electronic device 42 filters out the pulsation data from the spectrum data for obtaining pulseless spectrum data (step S208). In one embodiment, the electronic device 42 respectively filters out the pulsation vibration spectrum data, the pulsation voice spectrum data and the pulsation flow velocity spectrum data from the vibration spectrum data, the voice spectrum data and the flow velocity spectrum data for obtaining pulseless vibration spectrum data, pulseless voice spectrum data and pulseless flow velocity spectrum data.

Then, the electronic device 42 executes a frequency-domain-to-time-domain converting process to the pulseless spectrum data for obtaining pulseless time-domain data (step S210).

In one embodiment, the electronic device 42 executes the frequency-domain-to-time-domain converting process to the vibration pulseless spectrum data, the voice pulseless spectrum data and the pulseless flow velocity spectrum data for obtaining pulseless vibration time-domain data, pulseless voice time-domain data and pulseless flow velocity time-domain data.

Then, the electronic device 42 determines the evaluation index according to the pulseless time-domain data and the threshold data retrieved in the step S202 (step S212).

In one embodiment, the electronic device 42 determines the vibration evaluation index according to the pulseless vibration time-domain data and the vibration threshold data 430, determines the voice evaluation index according to the pulseless voice time-domain data and the voice threshold data 432, and determines the flow velocity evaluation index according to the pulseless flow velocity time-domain data and the flow velocity threshold data 434.

For example, if a range of the evaluation indexes is 1 to 10 (the index 10 representing that the possibility of blockade is higher, the index 1 representing that the possibility of blockade is lowest). The determined evaluation index is closer to 1 if the pulseless time-domain data is more similar as the threshold data, and is closer to 10 if the pulseless time-domain data is more dissimilar as the threshold data, and vice versa.

Thus, the present disclosed example can determine the accurate evaluation index.

In one embodiment, the electronic device 42 may further determine the whole evaluation index corresponding to the examination part according to the determined vibration evaluation index, the determined voice evaluation index and the determined flow velocity evaluation index.

Take the range of each evaluation index (namely, the vibration evaluation index, the voice evaluation index and the flow velocity evaluation index) is 1 to 10 (the index 10 representing that the possibility of blockade is higher, the index 1 representing that the possibility of blockade is lowest) for example. The electronic device 42 may determine the whole evaluation index is "abnormality" when all (or more than half) of evaluation indexes are negative indexes (such as any index between index 7 to index 10). The electronic device 42 may determine the whole evaluation index is "normality" when all (or more than half) of evaluation indexes are positive indexes (such as any index between index 1 to index 4). The electronic device 42 may determine the whole evaluation index is "unknown" when all (or more than half) of evaluation indexes are neutral indexes (such as any index between index 5 to index 6).

In one embodiment, the threshold data retrieved in the step S202 is spectrum data. Besides, in this embodiment, the electronic device 42 may not execute the step S210 and directly execute the step S212 to determine the evaluation index according to the generated pulseless spectrum data and the threshold data.

Figure 8:
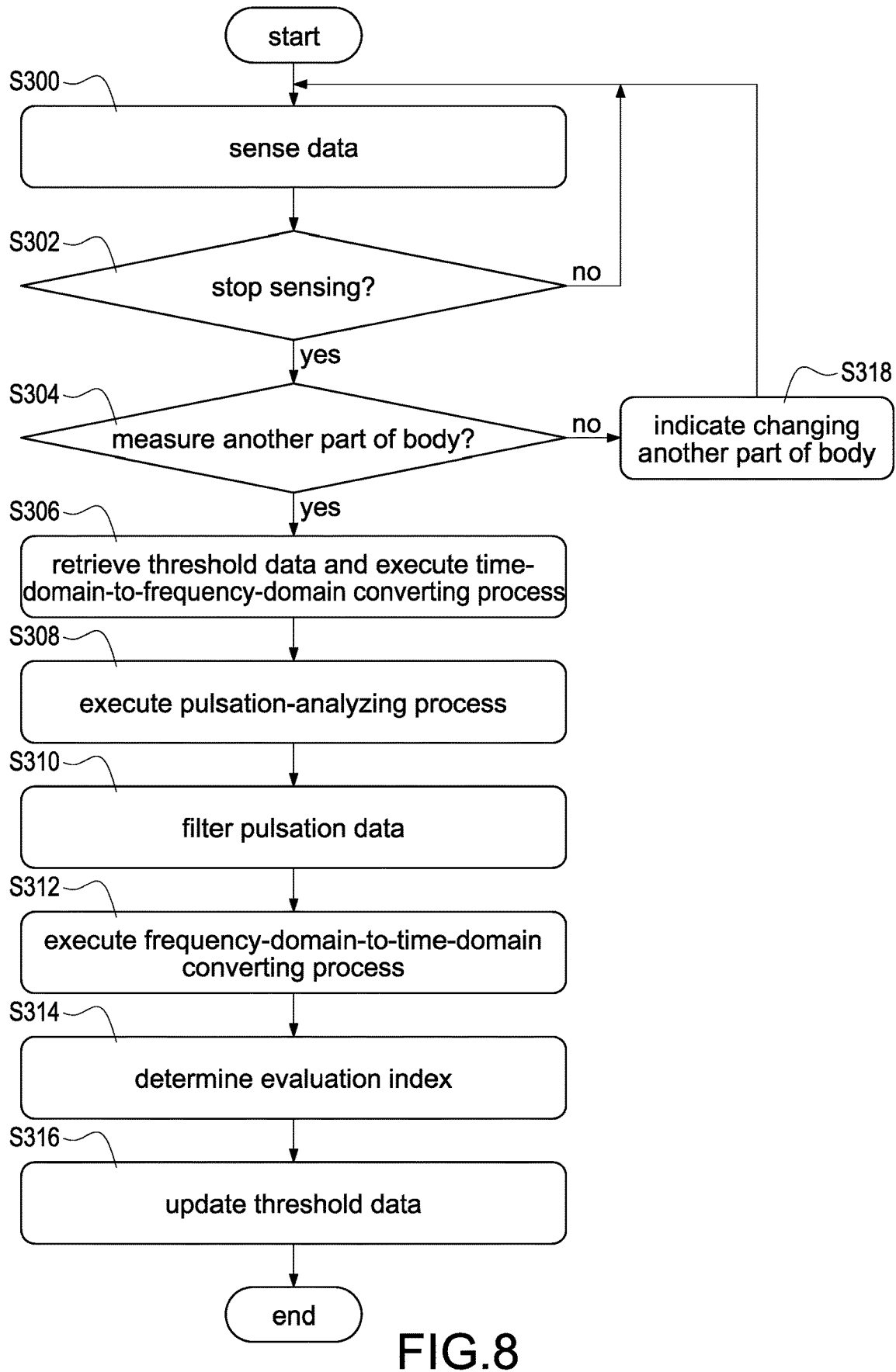
FIG. 8 is a flowchart of a method of monitoring vascular access status according to the first embodiment of the present disclosed example.

Please refer to FIG. 4 and FIG. 8 simultaneously. FIG. 8 is a flowchart of a method of monitoring vascular access status according to the first embodiment of the present disclosed example.

In the embodiment shown in FIG. 8, the monitor device 4 may measure a plurality of the vibration data respectively corresponding to multiple parts of the vascular access, determine the vibration evaluation index of each part of the vascular access, and further determine the whole vibration evaluation index of the vascular access according to the plurality of the vibration evaluation indexes.

Please be noted that although this embodiment is to determine the whole vibration evaluation index of the vascular access according to the plurality of the vibration evaluation indexes, but this specific example is not intended to limit the scope of the present disclosed example.

In the other embodiment, the monitor device 4 may measure a plurality of the vibration data, voice data and flow velocity data respectively corresponding to each part of the vascular access simultaneously, determine the vibration evaluation index, the voice evaluation index and the flow velocity evaluation index of each part of the vascular access, and further determine the whole vibration evaluation index, the whole voice evaluation index and the whole flow velocity evaluation index of the vascular access according to the plurality of the vibration evaluation indexes, the voice evaluation indexes and the flow velocity evaluation indexes.

In the embodiment shown in FIG. 8, the subject may first paste the measurement device on the first part of the vascular access for making the measurement device 40 sense the first vibration data of the first part of the vascular access via the vibration-sensing module 400 (step S300).

Then, the electronic device 42 determines whether the sense of this part is terminated (step S302), such as whether the part has been sensed for a default measurement time (for example, 10 seconds). If the electronic device 42 determines that the sense is not terminated, the electronic device 42 executes the step S300 again for continually sensing.

If the electronic device 42 determines that the sense is terminated, the electronic device 42 further determines whether all the parts had been measured (step S304). In one embodiment, the electronic device 42 determines that all the parts have been measured when determining that the multiple parts (such as the first part, the second part and the third part) of the vascular access of the subject have been measured and obtaining the sensed data of each part (such as the first vibration data, the second vibration data and the third vibration data).

If the electronic device 42 determines that any parts doesn't have been measured, the electronic device 42 generates an alert via the human-machine interface 428 for indicating the subject that changing the measurement part (step S318), and executes sense again after changing.

If the electronic device 42 determines that all the parts have been measured, the electronic device 42 executes the time-domain-to-frequency-domain converting process to the received sensed data for obtaining the corresponded spectrum data (step S306). In one embodiment, the electronic device 42 executes the time-domain-to-frequency-domain converting process to the first vibration sensed data, the second vibration sensed data and the third vibration sensed data for obtaining the first vibration spectrum data, the second vibration spectrum data and the third vibration spectrum data.

Then, the electronic device 42 executes the pulsation-analyzing process to the obtained spectrum data for obtaining pulsation data (step S308), and filters out the pulsation data from the spectrum data for obtaining pulseless spectrum data (step S310).

In one embodiment, the electronic device 42 executes the pulsation-analyzing process to the first vibration spectrum data, the second vibration spectrum data and the third vibration spectrum data for obtaining the first pulsation vibration spectrum data, the second pulsation vibration spectrum data and the third pulsation vibration spectrum data, and respectively filters out the first pulsation vibration spectrum data, the second pulsation vibration spectrum data and the third pulsation vibration spectrum data from the first vibration spectrum data, the second vibration spectrum data and the third vibration spectrum data for obtaining the first pulseless vibration spectrum data, the second pulseless vibration spectrum data and the third pulseless vibration spectrum data.

Then, the electronic device 42 executes the frequency-domain-to-time-domain converting process to the pulseless spectrum data which had filtered out the pulsation spectrum data for obtaining pulseless time-domain data (step S312). In one embodiment, the electronic device 42 executes the frequency-domain-to-time-domain converting process to the first pulseless vibration spectrum data, the second pulseless vibration spectrum data and the third pulseless vibration spectrum data for obtaining the first pulseless vibration time-domain data, the second pulseless vibration time-domain data and the third pulseless vibration time-domain data.

Then, the electronic device 42 determines the evaluation index according to the obtained pulseless time-domain data (step S314). In one embodiment, the electronic device 42 loads the first vibration threshold data, the second vibration threshold data and the third vibration threshold data from the memory 426, determines the first vibration evaluation index according to first pulseless vibration time-domain data and the first vibration threshold data, determines the second vibration evaluation index according to second pulseless vibration time-domain data and the second vibration threshold data, determines the third vibration evaluation index according to third pulseless vibration time-domain data and the third vibration threshold data.

Furthermore, the electronic device 42 further determines the whole vibration evaluation index of the vascular access according to the first vibration evaluation index, the second vibration evaluation index and the third vibration evaluation index.

Finally, the electronic device 42 updates the threshold data stored in the memory 426 according to the evaluation result (step S316).

In one embodiment, the electronic device 42 updates the data (such as the threshold data, the reference data and/or the history data) stored in the memory 426 for making the stored data (such as the stored threshold data, the stored reference data and the stored history data) is closer to the recent physiological characteristics of the subject via using the generated data (such as the first pulseless vibration time-domain data, the second pulseless vibration time-domain data and the third pulseless vibration time-domain data) according to the evaluation result (such as the first vibration evaluation index, the second vibration evaluation index and the third vibration evaluation index) determined this time.

Figure 5A:
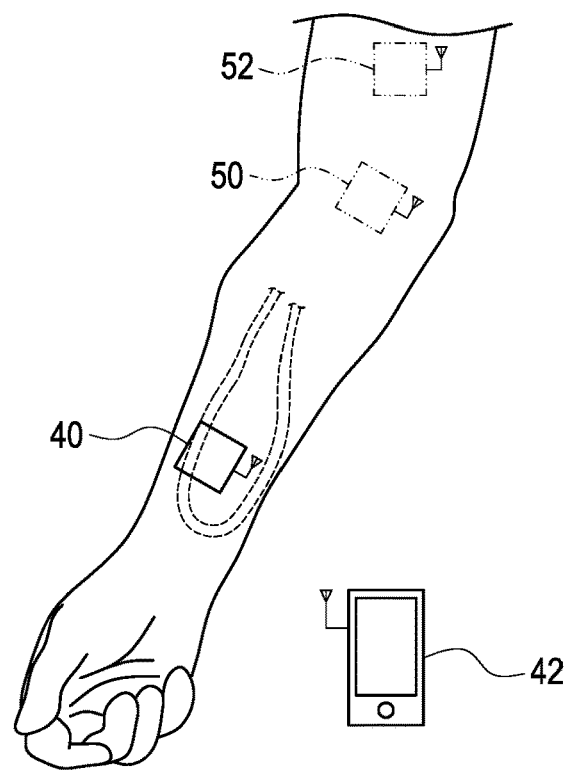
FIG. 5A is a schematic view of using a portable device for monitoring vascular access status over arteriovenous graft according to the fourth embodiment of the disclosed example.

Please refer to FIG. 4 and FIG. 5A simultaneously; FIG. 5A is a schematic view of using a portable device for monitoring vascular access status over arteriovenous graft according to the fourth embodiment of the present disclosed example.

In this embodiment, the monitor device 40 respectively retrieves the vibration data, the voice data and the flow velocity data induced by blood flow over the various parts of the subject, and executes comparison. Besides, the electronic device 42 is a smart phone installed the monitor module 420 (the monitor module 420 is an application program in this embodiment), and is wirelessly connected to the communication module 402 of the measurement device 40 via the transceiver 424 using Bluetooth communication technology.

As shown in FIG. 5A, when measurement, the subject may paste by himself/herself the measurement device 40 on the first part (for example, the position of the measurement device 40) of the vascular access of the subject for the first measurement time (such as 20 seconds) for making the measurement device 40 sense the first vibration data, the first voice data and the first flow velocity data induced by blood flow over the first part continually. And the measurement device 40 transfers the sensed first vibration data, the sensed first voice data and the sensed first flow velocity data to the electronic device 42 for analysis and process.

Then, the subject removes the measuring device 40 from the first part, and pastes the removed measurement device 40 on the second part (for example, the position 50 shown in FIG. 5A) of the vascular access of the subject for the second measurement time (such as 20 seconds) for making the measurement device 40 sense the second vibration data, the second voice data and the second flow velocity data induced by blood flow over the second part continually. And the measurement device 40 transfers the sensed second vibration data, the sensed second voice data and the sensed second flow velocity data to the electronic device 42 for analysis and process.

Then, the subject removes the measuring device 40 from the second part, and pastes the removed measurement device 40 on the third part (for example, the position 52 shown in FIG. 5A) of the vascular access of the subject for the third measurement time (such as 20 seconds) for making the measurement device 40 sense the third vibration data, the third voice data and the third flow velocity data induced by blood flow over the third part continually. And the measurement device 40 transfers the third second vibration data, the sensed third voice data and the sensed third flow velocity data to the electronic device 42 for analysis and process.

Finally, the electronic device 42 executes process to the received first vibration data, the received second vibration data, the received third vibration data, the received first voice data, the received second voice data, the received third voice data, the received first flow velocity data, the received second flow velocity data and the received third flow velocity data for determining the corresponded evaluation index.

Figure 5B:
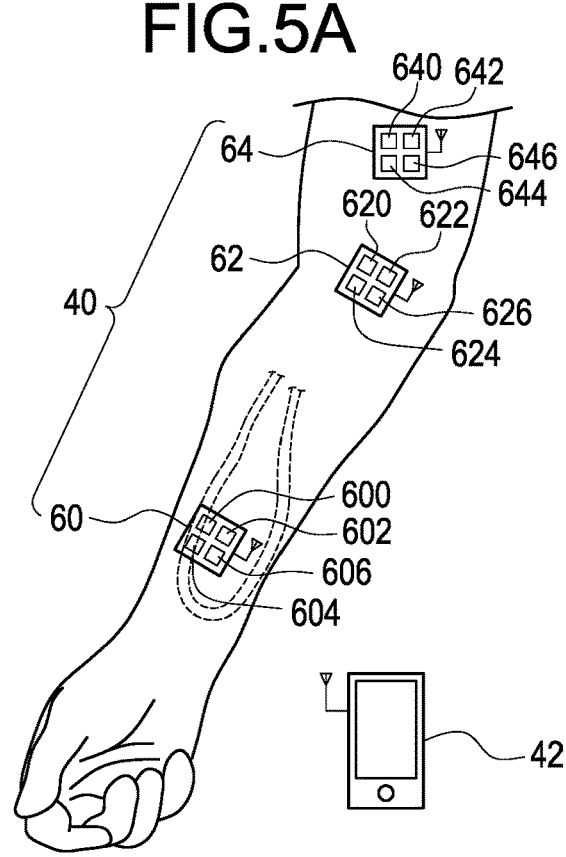
FIG. 5B is a schematic view of using a portable device for monitoring vascular access status over arteriovenous graft according to the fifth embodiment of the disclosed example.

Please refer to FIG. 4 and FIG. 5B simultaneously; FIG. 5B is a schematic view of using a portable device for monitoring vascular access status over arteriovenous graft according to the fifth embodiment of the present disclosed example. In this embodiment, the voice-receiving module comprises a first voice receiver 600, a second voice receiver 620 and a third voice receiver 640. The vibration-sensing module 400 comprises a first vibration sensor 602, a second vibration sensor 622 and a third vibration sensor 642. The communication module 402 comprises a first transmitter, a second transmitter 624 and a third transmitter 644. The blood-flow-velocity-sensing module 406 comprises a first blood-flow-velocity-sensing module 606, a second blood flow velocity sensor 626 and a third blood flow velocity sensor 646.

Besides, the monitor device 40 comprises a plurality of monitor patches 60-64. The monitor patch 60 comprises the first voice receiver 600, the first vibration sensor 602, the first transmitter 604, and the first blood flow velocity sensor 606. The monitor patch 62 comprises the second voice receiver 620, the second vibration sensor 622, the second transmitter 624, and the second blood flow velocity sensor 626. The monitor patch 64 comprises the third voice receiver 640, the third vibration sensor 642, the third transmitter 644, and the third blood flow velocity sensor 646.

As shown in FIG. 5B, when measurement, the subject may paste by himself/herself the monitor patch 60 on the first part of the vascular access of the subject, may paste by himself/herself the monitor patch 62 on the second part of the vascular access of the subject, and may paste by himself/herself the monitor patch 64 on the third part of the vascular access of the subject. Then, the subject waits for the default measurement time (such as 30 seconds) elapsing.

During waiting, the monitor patch 60 senses the first voice data via the first voice receiver 600, senses the first vibration data via the first vibration sensor 602, senses the first flow velocity data via the first blood flow velocity sensor 606, and transfers the sensed data to the electronic device 42 for analysis and process via the first transmitter 604. Similarly, the monitor patch 62 senses the second voice data via the second voice receiver 620, senses the second vibration data via the second vibration sensor 622, senses the second flow velocity data via the second blood flow velocity sensor 626, and transfers the sensed data to the electronic device 42 for analysis and process via the second transmitter 624. The monitor patch 64 senses the third voice data via the second voice receiver 640, senses the third vibration data via the second vibration sensor 642, senses the third flow velocity data via the second blood flow velocity sensor 646, and transfers the sensed data to the electronic device 42 for analysis and process via the third transmitter 644.

Finally, the electronic device 42 executes process to the received data and determines the evaluation index.

The present disclosed example can effectively reduce the measurement time via using the multiple monitor patches to measure.

Please be noted that although the devices shown in FIG. 5A and FIG. 5B are used in the vascular access comprising the arteriovenous graft, the devices may also be used in the vascular access comprising arteriovenous fistula, this specific example is not intended to limit the scope of the present disclosed example.

The above mentioned are only preferred specific examples in the present disclosed example, and are not thence restrictive to the scope of claims of the present disclosed example. Therefore, those who apply equivalent changes incorporating contents from the present disclosed example are included in the scope of this application, as stated herein.

What is claimed is:

1. A portable device for monitoring vascular access status, comprising:
 a measurement device, comprising:
  at least one monitor patch, comprising:
   a patch structure used to removably paste over a subject;
   a vibration-sensing module used to configured to sense first vibration data induced by blood flow over a first part of a vascular access of the subject when the at least one monitor patch is pasted over the first part, and sense second vibration data induced by blood flow over a second part of the subject when the at least one monitor patch is pasted over the second part;
   a voice-receiving module used to sense first voice data induced by blood flow over the first part when the at least one monitor patch is pasted over the first part, and sense second voice data induced by blood flow over the second part when the at least one monitor patch is pasted over the second part;
   a blood-flow-velocity-sensing module used to sense first flow velocity data induced by blood flow over the first part when the at least one monitor patch is pasted over the first part, and sense second flow velocity data induced by blood flow over the second part when the at least one monitor patch is pasted over the second part; and
  a communication module electrically connected to the at least one monitor part and used to transmit data to an electronic device; and
 a monitor module used to configured to control the electronic device connected to the communication module of the measurement device to load first vibration threshold data corresponding to the first part, second vibration threshold data corresponding to the second part, voice threshold data and flow velocity threshold from a memory, determine a first vibration evaluation index corresponding to a status of the first part according to the first vibration data and the first vibration threshold data, determine a second vibration evaluation index corresponding to a status of the second part according to the second vibration data and the second vibration threshold data, determine voice evaluation index according to the first voice data, the second voice data and the voice threshold data, determine flow velocity evaluation index according to the first flow velocity data, the second the flow velocity data and the flow velocity threshold data, and determine a whole vibration evaluation index according to the first vibration evaluation index, the second vibration evaluation index, the voice evaluation index and the flow velocity evaluation index.

2. The portable device for monitoring vascular access status according to claim 1, wherein the first vibration threshold data and the second vibration threshold data are amplitude values, the monitor module determines that the first vibration evaluation index is a negative index when a maximum or an average of a plurality of vibration amplitudes of the first vibration data is less than the first vibration threshold data, the second vibration evaluation index is the negative index when a maximum or an average of a plurality of vibration amplitudes of the second vibration data is less than the second vibration threshold data.

3. The portable device for monitoring vascular access status according to claim 1, wherein the monitor module is configured to execute a time-domain-to-frequency-domain converting process to the first vibration data and the second vibration data for obtaining first vibration spectrum data and second vibration spectrum data, execute a pulsation-analyzing process to the first vibration spectrum data and the second vibration spectrum data for obtaining first pulsation vibration spectrum data and second pulsation vibration spectrum data, filter out the first pulsation vibration spectrum data and the second pulsation vibration spectrum data respectively from the first vibration spectrum data and the second vibration spectrum data for obtaining first pulseless vibration spectrum data and second pulseless vibration spectrum data, determine the first vibration evaluation index according to the first pulseless vibration spectrum data and the first vibration threshold data, and determine the second vibration evaluation index according to the second pulseless vibration spectrum data and the second vibration threshold data.

4. The portable device for monitoring vascular access status according to claim 3, wherein the monitor module is configured to execute a frequency-domain-to-time-domain converting process to the first pulseless vibration spectrum data and the second pulseless vibration spectrum data for obtaining first pulseless vibration time-domain data and second pulseless vibration time-domain data, determine the first vibration evaluation index according to the first pulseless vibration time-domain data and the first vibration threshold data, and determine the second vibration evaluation index according to the second pulseless vibration time-domain data and the second vibration threshold data.

5. The portable device for monitoring vascular access status according to claim 1, wherein the memory stores a plurality of vibration reference data, the monitor module selects two of the plurality of the vibration reference data as the first vibration threshold data and the second vibration threshold data according to a set of physiological parameters of the subject.

6. The portable device for monitoring vascular access status according to claim 1, wherein the memory stores vibration history data of the subject, the monitor module is configured to load the vibration history data of the subject as the first vibration threshold data and the second vibration threshold data.

7. The portable device for monitoring vascular access status according to claim 1, wherein the voice-receiving module is a microphone, the vibration-sensing module is an accelerometer, the blood-flow-velocity-sensing module is an optical flow velocity meter, the communication module is a Bluetooth network module.

8. The portable device for monitoring vascular access status according to claim 1, wherein the memory stores a plurality of voice reference data, the monitor module is configured to selects one of the plurality of the voice reference data as the voice threshold data according to a set of physiological parameters of the subject.

9. The portable device for monitoring vascular access status according to claim 1, wherein the memory stores a plurality of flow velocity reference data, the monitor module is configured to selects one of the plurality of the flow velocity reference data as the flow velocity threshold data according to a set of physiological parameters of the subject.

10. The portable device for monitoring vascular access status according to claim 1, wherein the memory stores voice history data of the subject, the monitor module is configured to load the voice history data of the subject as the voice threshold data.

11. The portable device for monitoring vascular access status according to claim 1, wherein the memory stores flow velocity history data of the subject, the monitor module is configured to load the flow velocity history data of the subject as the flow velocity threshold data.

12. The portable device for monitoring vascular access status according to claim 1, wherein the at least one monitor patch is used to be pasted over one of the first part and the second part for measurement, be teared out and be pasted over another of the first part and the second part for measurement.

13. The portable device for monitoring vascular access status according to claim 1, wherein the first part is either an arteriovenous fistula or an arteriovenous graft, the second part is either veins or arteries outside the first part.

14. The portable device for monitoring vascular access status according to claim 13, wherein the measurement device comprises at least two of the monitor patches, two of the monitor patches are respectively pasted over the first part and the second part for simultaneously measuring blood flow of the first part and the second part.

15. The portable device for monitoring vascular access status according to claim 1, wherein when the at least one monitor patch is pasted over the third part, the vibration-sensing module is further configured to sense third vibration data induced by blood flow over a third part of the subject, the voice-receiving module is further configured to sense third voice data induced by blood flow over the third, and the voice-receiving module is further configured to sense third flow velocity data induced by blood flow over the third part;

wherein the monitor module is further configured to load third vibration threshold data from the memory, determine a third vibration evaluation index corresponding to a status of the third part according to the third vibration data and the third vibration threshold data, determine the voice evaluation index according to the first voice data, the second voice data, the third voice data and the voice threshold data, determine the flow velocity evaluation index according to the first flow velocity data, the second the flow velocity data, the third flow velocity data and the flow velocity threshold data, and determine the whole vibration evaluation index according to the first vibration evaluation index, the second vibration evaluation index, the third vibration evaluation index, the voice evaluation index and the flow velocity evaluation index.

* * * * *